(12) United States Patent
Joshi

(10) Patent No.: US 8,728,521 B2
(45) Date of Patent: May 20, 2014

(54) PHYSICALLY/MOLECULARLY DISTRIBUTED AND/OR CHEMICALLY BOUND MEDICAMENTS IN EMPTY, HARD CAPSULE SHELLS

(75) Inventor: Hemant Narahar Joshi, Parsippany, NJ (US)

(73) Assignees: Hemant N. Joshi, Parsippany, NJ (US); Tara Innovations LLC, Parsippany, NJ (US)

( * ) Notice: Subject to any disclaimer, the term of this patent is extended or adjusted under 35 U.S.C. 154(b) by 334 days.

(21) Appl. No.: 12/841,008

(22) Filed: Jul. 21, 2010

(65) Prior Publication Data
US 2010/0285116 A1 Nov. 11, 2010

Related U.S. Application Data

(63) Continuation of application No. 11/306,398, filed on Dec. 27, 2005, now abandoned.

(51) Int. Cl.
*A61K 9/20* (2006.01)

(52) U.S. Cl.
USPC .......................................................... 424/464

(58) Field of Classification Search
None
See application file for complete search history.

(56) References Cited

U.S. PATENT DOCUMENTS

| | | | |
|---|---|---|---|
| 4,510,168 A | | 4/1985 | Sakashita et al. |
| 4,532,881 A | | 8/1985 | Sakashita et al. |
| 4,623,629 A | * | 11/1986 | Kerschensteiner ........... 436/518 |
| 5,672,359 A | * | 9/1997 | Digenis et al. ................ 424/463 |
| 5,756,123 A | * | 5/1998 | Yamamoto et al. ........... 424/451 |
| 6,752,953 B2 | * | 6/2004 | Chen et al. .................... 264/330 |
| 7,666,398 B2 | | 2/2010 | Uhrich |
| 2003/0104062 A1 | | 6/2003 | Bemer et al. |
| 2003/0161872 A1 | * | 8/2003 | Chen et al. .................... 424/452 |
| 2004/0146559 A1 | | 7/2004 | Sowden et al. |
| 2005/0142186 A1 | | 6/2005 | Hayakawa et al. |
| 2006/0275361 A1 | * | 12/2006 | Sakanishi et al. ............. 424/456 |
| 2007/0141137 A1 | * | 6/2007 | Nagahara et al. ............. 424/451 |
| 2008/0248102 A1 | | 10/2008 | Rajewski et al. |
| 2008/0274187 A1 | | 11/2008 | Cao |
| 2010/0168410 A1 | | 7/2010 | Cade et al. |
| 2011/0171275 A1 | * | 7/2011 | Jiang et al. .................... 424/400 |

FOREIGN PATENT DOCUMENTS

| | | |
|---|---|---|
| WO | WO1997004755 | 2/1997 |
| WO | WO 2010020098 A1 * | 2/2010 |

OTHER PUBLICATIONS

Eccles, (Efficacy and Safety of an antiviral Iota-Carragennan nasal spray: a randomized double-blind, placebo-controlled exploratory study in volunteers with early symptoms of the common cold, Respiratory Research 2010, 11(108), 1-10.*

Ganzalez, Polysaccharides as Antiviral Agents: Antiviral Activity of Carrageenan, Antimicrobial Agents and Chemotherapy, 1987, 31(9), 1388-1393.*

(Continued)

*Primary Examiner* — Paul Dickinson

(57) ABSTRACT

The present invention incorporates medicaments in the empty hard capsule shells (body and cap). The medicament is either physically/molecularly distributed and/or chemically bound to the polymer matrix of the capsule shell composition. Other medicaments in the form of drug-loaded matrices (powders, granules, beads, pellets, mini-tablets, and mini-capsules) can be filled in the drug-loaded empty, hard capsule shells. The same capsule dosage form contains medicaments in the core matrix and in the shell.

4 Claims, 5 Drawing Sheets

(56) References Cited

OTHER PUBLICATIONS

McConville, J.T., Ross, A.C., Chambers, A.R., Smith, G. Florence, A. J., and Stevens, H.N.E., The effect of wet granulation on the erosion behaviour of an HPMC-lactose tablet, used as a rate controlling component in a pulsatile, Eur. J. Pharm & Biopharm 57 : 541-549 (2004).

Joshi, H.N., Recent advances in drug delivery systems : Polymeric prodrugs, Pharm. Tech., 12 : 118, 120, 122, 124, 126, 128, and 130 (1988).

* cited by examiner

PHYSICALLY/MOLECULARLY DISTRIBUTED AND/OR CHEMICALLY BOUND MEDICAMENTS IN EMPTY, HARD CAPSULE SHELLS

CROSS-REFERENCE TO RELATED APPLICATIONS

This application is a continuation of U.S. patent application Ser No. 11/306,398 filed on Dec. 27, 2005 now abandoned and titled "PHYSICALLY/MOLECULARLY DISTRIBUTED AND/OR CHEMICALLY BONDED MEDICAMENTS IN CAPSULE SHELLS"

BACKGROUND OF THE INVENTION

Combination drug therapy has been gaining a lot of importance in recent times. The reasons could be—avoidance of taking multiple tablets/capsules per day, savings on co-payment for different medicines and assurance of patient compliance to drug therapies. It is important to show that different drugs combined in the same dosage form should be stable during manufacture and storage and should not interact physically or chemically with each other or with excipients to produce degradation products. Each drug in the combination dosage form should show the desired release rate from the dosage form to get absorbed in sufficient quantities upon oral administration or release the drug to surrounding environment in case of other delivery routes.

Pharmaceutical capsule dosage forms are widely used in delivering drugs. The main two types of capsules are—hard shell capsules and soft shell capsules. The present patent relates to hard shell capsules. The capsules are normally prepared using gelatin and normally termed as hard gel capsules. In recent times, several polymers have been employed to manufacture hard shell capsules. In 1977, Christen and Cheng patented (U.S. Pat. No. 4,026,986) hard shell capsules manufactured using hydroxyalkyl starch. WO 1997004755 (International application #: PCT/EP1996/003263) prepared hard gelatin capsules with internal or external polymer coating using the double dipping technique. The inventors used polyvinyl alcohol and polyvinyl acetate polymers along with necessary additives.

Gennadios invented non-gelatin capsules (U.S. Pat. No. 6,214,376) comprising k-carrageenan, water-soluble plasticizer, and dextrins. The composition also included hydrolyzed starch as a variation. U.S. Pat. No. 6,517,865 claimed hard and soft capsules comprising of water-soluble cellulose ethers, hydrocolloids and sequestering agents. The capsules also comprised of a coating with polymers including cellulose acetate phthalate, hydromellose phthalate etc. In 2004 patent by Chen et al. (U.S. Pat. No. 6,752,953), authors described the usage of other polymers such as cellulose derivatives including cellulose, cellulose ester, methyl cellulose, hydroxypropyl methyl cellulose etc., acrylates including polyacrylate, polymethylacrylate, poly (methacrylate-methylmethacrylate) etc., and polyolefins including polyethylene, polypropylene, polyvinyl chloride, polyvinyl alcohol etc. to prepare capsules.

US patent application #2005/0142186 used low-substituted cellulose ether to produce hard capsules. The inventors also proposed a method for capsule preparation. The pins were dipped in the alkaline solution of low-substituted cellulose ether followed by dipping in an aqueous acid solution to form a gel (low-substituted cellulose ethers are soluble in alkaline medium and forms a gel in the acidic environment). The pins covered with the gel are further washed with water before the drying step. U.S. Pat. No. 6,949,256 used a mixture of kappa carrageenan and iota carrageenan. Kappa carrageenan is known to form a strong gel in the presence of potassium cations. However, these tend to be brittle and exhibit syneresis (exudating of liquid portion of the gel). Iota carrageenan tends to react with calcium cations and forms a weaker and more flexible gel.

A US patent application #2008/0,248,102 by Rajewski and Haslam prepared hard shell capsules with pullulan, a plasticizer and a dissolution-enhancing agent. The capsules were meant to dissolve in the mouth cavity (orally dissolving capsules). US patent application #2008/0,274,187 prepared hard capsule compositions comprising carrageenan, locust bean gum, xanthan gum, sorbitol, and pullulan. These capsules eliminated the problem of cracking, embrittlement, chipping and deformation due to water loss and mechanical stress. US patent application #2010/0,168,410 described a composition of hard capsules of hydroxypropyl methyl cellulose and the process of dip-coating manufacture. The dipping pins were heated at 55-95° C. and the polymer solution was maintained at 1 to 10° C. below its gelling temperature.

McConville et al. (Eur. J. Pharmaceutics & Biopharm. 57: 541-549 (2004) prepared a capsule filled with low-substituted hydroxypropyl cellulose on which a propranolol tablet was placed followed by an erodible tablet containing HPMC and lactose manufactured by either direct and wet granulation technique. The body of the capsule was precoated with insoluble ethyl cellulose suggesting the drug release only after the dissolution of the cap of the capsule. In this case, the capsule shell was not loaded with the drug—propranolol.

In the US patent application #2004/0,146,559, a film forming shell was formed on the inside core containing the active ingredient. The shell may have different properties to alter the drug release rates. In this patent, the core and the shell were manufactured in situ. In the present invention, the empty hard capsule shell containing the drug is produced by the manufacturer of capsules (such as Capsugel, Universal capsules, and Shionogi capsules).

In the U.S. Pat. No. 6,709,427, microsphere preparation was the core technology in which the microspheres were encapsulated to produce microcapsules. This is a totally different kind of drug delivery technique compared to the present patent application using empty, hard capsule shell in which the drug granules or powder are filled in the capsule shell body.

In the US patent application #2003/0,104,062, the capsules core is loaded with the drug. The shell surrounding the drug-containing core governed the release rate (zero order) of the drug by diffusion mechanism due to its swelling. The shell also promoted gastric retention of the capsules by swelling upon the imbibation of gastric fluid to a size that is retained in the stomach during the fed mode. In one embodiment, no drug was incorporated in the capsule shell composition. In another embodiment, the drug was incorporated in the shell to produce a burst effect. In this case, the same drug was incorporated in the core and in the shell/casing. In this patent, the preparation of capsule shell was part of the manufacturing process in situ. The desired zero order release and the manufacturing process are the two key differences between US patent application #2003/0104062 and the current patent application.

The subject of polymeric prodrugs has been studied widely. A review article (Joshi, H., Pharm. Tech., 12: 118, 120, 122, 124, 126, 128 and 130, (1988)) has summarized different types of polymeric drug delivery systems. U.S. Pat. No. 7,056,500 provided details developing a hydrolytically stable linkage between an opioid antagonist and poly (ethylene glycol). Choe and Greenwald described a method of making and using thiol-linked polymeric prodrugs (U.S. Pat. Nos. 7,262,164). 7,666,398 demonstrated the usage of polyanhydrides as a polymer backbone to prepare polymeric prodrugs. The low molecular weight drugs used with this method included one carboxylic acid group and at least one amine, thiol, alcohol or phenol group within its structure.

There are mainly two methods to prepare empty hard shell capsules: pin dip-coating and heat-melting. A liquid mass is produced by dissolving the capsule compositions in a solvent system or by melting at an appropriate temperature. In the pin dip-method, a plurality of pins maintained at a certain temperature dip in the solution and is withdrawn at a pre-determined rate while spinning. The pins coated with capsule composition are then dried at a gradual rate at a suitable temperature. The body and cap of the capsules are separated from the pins and then trimmed to an exact length. The method has been employed to prepare the body and cap of the capsules. The body and cap are joined together and a logo is printed, if necessary.

InnerCap, a UK-based company proposed combination capsules in which a capsule may contain another small capsule or a tablet along with granules. The granules may be made up of beads or other forms, which may contain more than one type of drug molecules. This way, more than one type of drug may be combined in the same capsule. However, all the drugs reside in the capsule core and there is no drug in the capsule shell composition.

SUMMARY OF THE INVENTION

The present invention proposes a design to incorporate medicaments or drugs in the capsule shells (body and cap). Medicaments in the cap and body of the capsules may be different. Other medicaments in the form of granules, beads etc. can be filled in the capsules, which may contain medicaments capsule shell. Thus, the same capsule may contain medicaments in the core matrix and in the shell. The key advantage of incorporation of drug in the shell is to obtain a desired rate of release of the medicament, mainly for potent drugs. Other advantage is to produce a combination drug delivery system. The concept can be used for the hard gelatin, hard non-gelatin, soft gelatin and soft non-gelatin capsules. The type of medicaments can be from any class, but should be low-dose medicaments. The medicament has to be stable in the capsule shell during manufacture and during appropriate storage conditions for the capsules.

The present invention proposes a new way of combining a plurality of drugs in the capsule formulations so that the release rate of each drug can be controlled to a desired value. The empty hard capsule shells, in which the active ingredient is physically/molecularly distributed and/or chemically bound in capsule shell composition, are then used further to manufacture pharmaceutical capsule formulations by filling them with drug-loaded powder, granules, beads, mini-tablets, pellets and mini-capsules. In one embodiment, the drug is dissolved in the capsule shell forming composition. In another embodiment, the drug, which is insoluble in the shell-forming composition, is physically dispersed or suspended. In yet another embodiment, the drug is chemically bound to the polymer used in the capsule-shell composition. The capsules are prepared by pin dip-coating or heat-melting methods. The polymers that can be used in making the present empty, hard capsule shells can be divided into the following groups: 1) Cellulose- or cellulose compounds, which include, but are not limited to, cellulose, cellulose ether, methyl cellulose, hydroxypropyl methyl cellulose, hydroxypropyl cellulose, hydroxyethyl cellulose, carboxymethyl cellulose, cellulose acetate phthalate, 2) starch-based compounds, which include, but not limited to hydroxyethyl starch, hydroxypropyl starch, hydroxyethyl methyl starch, 3) carrageenans—kappa and iota , 4) Acrylate compounds, which include, but not limited to, polyacrylate, polymethylacrylate, poly(acrylate-methylacrylate), poly(methylacrylate-methyl methacrylate), 5) polyolefins, which include, but limited to, polyvinyl chloride, polyvinyl alcohol, and polyvinyl acetate and 6) pullulan (a polysaccharide polymer consisting of maltotriose units). The empty, hard capsule shell can also be a laminate where the drug-loaded layer is either inner or outer. The non-drug loaded layer can have a function such as, an enteric coated layer or a layer to control drug diffusion as a result of swelling. The following are the key words used and the definition of various terms applicable to this patent application.

A "Capsule dosage form" is defined as a delivery system for an active moiety and which is prepared with a suitable material or matrix such as gelatin or a polymer to form a capsule shell.

A "capsule shell" is referred to as a film-forming composition used to encapsulate an active moiety in a capsule dosage form.

The word "encapsulate" is defined as the act of placing the composition containing a therapeutically effective amount of an active moiety inside the film-forming composition, such that the core material is completed surrounded by the film-forming material.

A "medicament" is an agent that promotes recovery from an ailment or an injury. Similar words to medicament are medicines, drugs, therapeutic agent, biologically active molecule/agent and an active moiety. These agents affect physical and/or biochemical properties of a biological system. The classes of medicament applicable in this invention include, but not limited to, anti-tumor agents, cardiovascular drugs, hormones, growth factors, steroidal agents, anti-viral agents, antibiotics and the like.

The "therapeutically effective amount" is the amount of pharmaceutical or nutraceutical medicament needed to treat, totally or partially, a disease state or alleviates one or more symptoms of the condition.

The "empty, hard capsule shell" as name suggests is hard, durable and smooth. It retains its shape and it is dry in nature. As evident from the word "empty", there is nothing inside core portion of the capsule shell. The capsule shell is prepared using a film-forming composition/matrix. The hard capsule shell comprises of two parts—a body in the core of which holds the contents of the dosage form, such as, powders/granules/beads/pellets/a mini-tablet/a mini-capsule and a cap, which fits on the body of the capsule shell and acts as a cover (U.S. Pat. Nos. 4,510,168 and 4,532,881). Someone may argue that the body of a capsule is type of a core. However, people working in the field of pharmaceutical formulations will not confuse the "body" of the capsule shell with the material within the cores of the capsule. Mini-tablets or mini-capsules refer to small drug-loaded dosage forms which will fit in easily in the drug-loaded hard capsule shell described in the present inventions.

The "drug-loaded empty, hard capsule shells" means the empty, hard capsule shells in which a drug is either physically or molecularly embedded in the shell and/or chemically bound to the polymeric material incorporated in the capsule shell composition. When the drug is physically embedded in the shell, the drug is in a suspended or dispersed state. The term "molecularly embedded" means, the drug is in a dissolved state in the shell. The chemically bound drug is covalently bound to the polymer backbone in the capsule shell composition. The drug is either directly bound to the polymer or through a linkage or linker. The drug is released from the polymeric prodrug via hydrolysis or enzymatic degradation.

DETAILED DESCRIPTION

A hard capsule dosage form is manufactured by filling the core of the hard capsule shell with powders, granules, beads, pellets, a tablet or another capsule. In the recent times, scientists have started filling the hard capsule shells with liquids too. Currently, the hard capsule shells are prepared with either gelatin or hydroxypropyl methyl cellulose. The hard capsule shells are purchased from the capsule suppliers. There are main three manufacturers of hard capsule shells—Capsugel, Shionogi and Universal capsules. Each capsule has two parts—a body and the cap. As mentioned in the background section, several new types of polymeric substances have been used to manufacture empty, hard capsule shells. These are—cellulosic compounds, acrylates, starch ethers, polyolefins, pullulans, and carrageenans. Apart from the main constituent of the capsule shell being gelatin or polymeric in nature, the shell also contains other excipients such as plasticizers (e.g., polyethylene glycol, sorbitol, glycerol), stabilizers (antimicrobial and antioxidants), colorants (FD&C colors, titanium dioxide, natural dyes including riboflavin, carotenes, turmeric and caramel) and sequestering agents (citric acid, sodium citrate, and ethylenediaminetetraacetic acid).

The rate of capsule dissolution in a desired media governs the release of medicaments residing the core of the capsule. The rate of release can be altered using a combination of polymers in the capsule composition.

The present invention proposes a method to develop a combination hard capsule dosage form in which the medicament resides in the core of the capsule as well as in the hard capsule shell itself. The incorporation of medicaments in the capsule shell core is a prior art. Thus, the core of the present invention is to incorporate medicaments in the empty, hard capsule shells. The medicament in the hard capsules shell is either physically or molecularly dispersed and/or chemically bound to the polymeric material of the capsule shell. In one embodiment, the body and the cap of the hard capsule shell contain the same active moiety. In another embodiment, the medicament resides only in the cap or the body of the capsule shell. In yet another embodiment, different medicaments are incorporated in the body and the cap of the hard capsule shell. In yet another embodiment, a combination of medicaments is incorporated in the body and the cap of the hard capsule shells.

Figure 1:
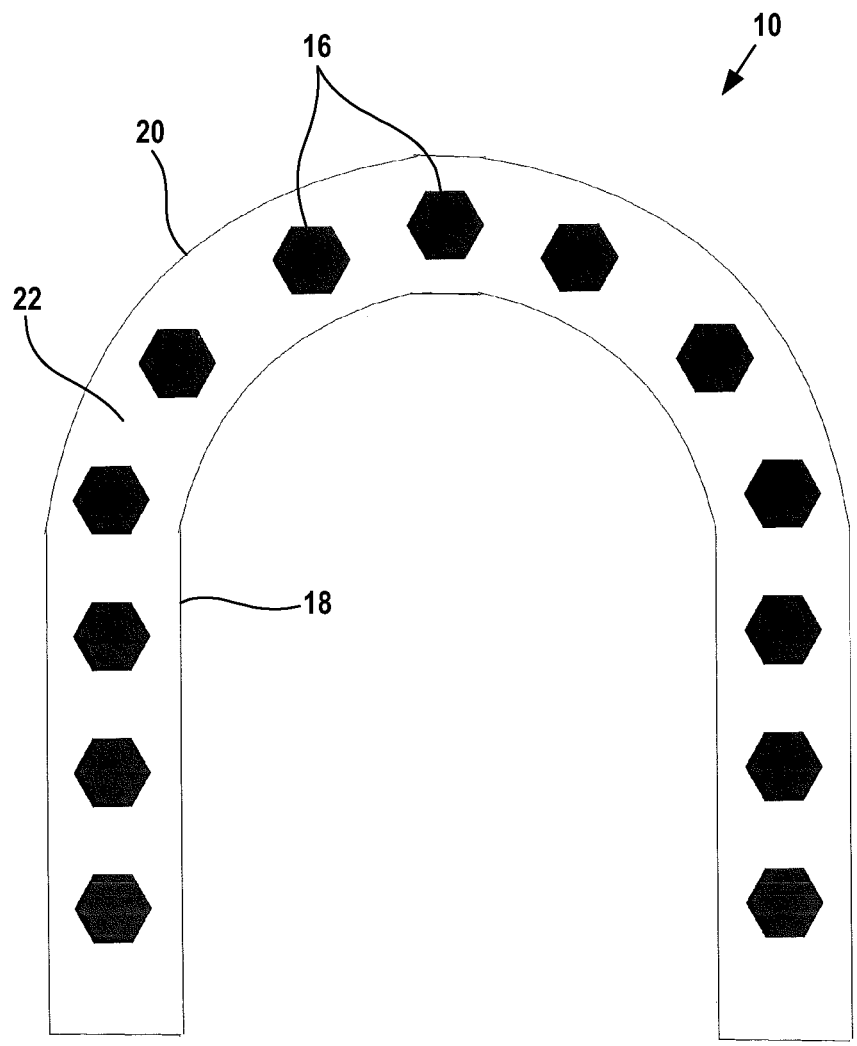
FIG. 1 illustrates the cap of a hard-shell capsule with drug molecules of a first drug dispersed throughout the cap and a second drug inside the capsule.

FIG. 1 depicts a capsule cap 10 that cooperatively engages a capsule body 12 to form a hard-shell capsule 14 (see FIG. 2) in accordance with the present invention. The cap 10 has drug molecules 16 disbursed throughout the cap 10 between a cap inner surface 18 and a cap outer surface 20. The capsule body 12 in the illustrated embodiment of the capsule 14 has a similar structure, that is, a drug dispersed throughout the capsule body 12 between inner and outer surfaces of the capsule body.

The composition 22 of the capsule cap 12 (or the capsule body 14) may consist of gelatin, HPMC, cellulose-derivatives, acrylates, polyolefins, vinyl polymers and other polymeric systems used in forming caps and bodies of conventional hard-shell capsules. The main constituent of the composition 22 of the capsule shell (body or cap) may be a combination of polymers mentioned above. The shell composition 22 (body or cap) may also contain other excipients such as plasticizers, emulsifiers, stabilizers, colorants etc. The rate of capsule dissolution in a desired media or location within the body may be altered using selected combination of the capsule composition 22 as is known in the art.

The medicament or drug 16 can be physically or molecularly dispersed throughout the composition 22 of the cap 10 or body 12. The drug or medicament 16 in the powder form can be physically dispersed in the capsule composition 22. The medicament or drug 16 may be dissolved in the capsule composition 22 to disperse the drug 16 at a molecular level. The medicament or drug 16 may form an ion-pair bond with the groups in the polymer or the excipients used to prepare the capsule composition 22. The medicament or drug 16 may form a chemical bond with the polymer or the excipients used to prepare the capsule composition 22. The chemical bond can be of any nature peptide, an ester or other kinds.

Figure 2:
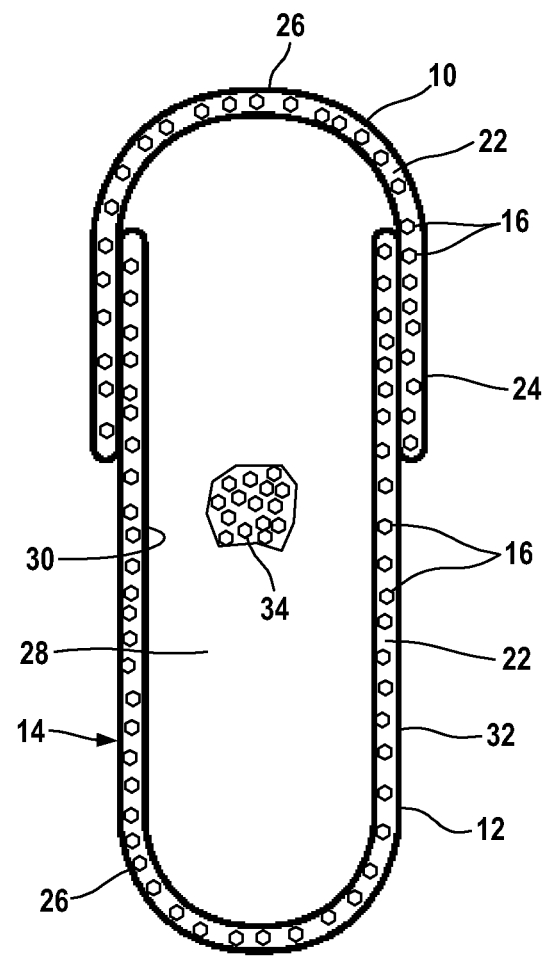
FIG. 2 illustrates the capsule formed from the cap shown in FIG. 1 and a similar body.

FIG. 2 illustrates a capsule 14 in which an identical drug 16 is dispersed throughout the composition 22 forming each of the cap 10 and the body 12. The cap 10 and the body 12 have respective open ends 24 and respective closed ends 26. The open ends 24 of the cap 10 and body 12 telescopically overlap one another as is known in the hard-shell capsule art to form the capsule 14. The capsule 14 defines a hollow interior space or volume 28 surrounded by an inner surface 30 of the capsule 14 and has an outer surface 32.

In other possible embodiments of the present invention, only one of the cap 10 and the body 12 includes the drug 16 dispersed throughout the cap or body. In yet other embodiments of the present invention the cap 10 and the body 12 may contain different drugs 16.

Another drug or drugs or pharmaceutical materials 34 may optionally be placed within the space or volume 28 during assembly of the capsule 14 to deliver such other pharmaceutical materials 34 to the location where the capsule 14 dissolves in the body. The capsule inner surface 30 may optionally be coated with a film or coating 36 deposited on the surface 30. See FIG. 3 which illustrates the coating 36 deposited on the inner surface of the cap 10. The capsule outer surface 32 may optionally be coated with a film or coating 38 deposited on the surface 32. See FIG. 4, which illustrates the coating 38 deposited on the outer surface of the cap 10. The inner film or coating 36 may include a yet additional drug intended for delivery to the location where the capsule 14 dissolves in the body. The outer film or coating 38 may be an enteric coating as is known in the hard-capsule shell art or may include a further additional drug to be delivered by the capsule 14.

Using the present invention, the hard capsule shell manufacturer will manufacture the capsule shells containing a medicament(s) and supply to a pharmaceutical company which intends to develop a capsule dosage form. The pharmaceutical company, purchasing the hard capsule shells, will produce a suitable composition (such as drug-loaded powders, drug-loaded granules etc.) of the core material and fill in the drug-loaded hard capsule shells.

There are various sizes of hard capsule shells available ranging from sizes '000' to '5' (higher the number, smaller is the dose volume), the most commonly used are sizes '0' and '1'. The fill weight of granules having a density of 0.7 g/mL is 475 mg and 350 mg for size '0' and '1' capsules, respectively. Size '000' capsules can contain 960 mg of core material loaded with medicament. The average weights of size '1' and '0' empty hard gelatin capsule shell are 76 mg and 96 mg, respectively. The drug loading itself can affect the properties of the capsule shell and as a result, the amount of drug loaded in the empty, hard capsule shell is limited. In general, only potent drugs can be loaded in empty, hard capsule shells. One skilled in the art of formulation will determine the stability of the drug in the capsule shell composition during manufacture and storage. It is important to establish the desired release rate of medicament embedded in the shell under pre-determined conditions such as in the acidic and basic media, and in the presence of bile acids/food etc. The polymer for the empty, hard capsule shell and the drugs (to be incorporated in the capsule shell matrix) need to be selected judiciously.

Bioavailability of a drug constitutes two features—the rate and the extent of absorption. For potent drugs with narrow therapeutic indices, it is critical to maintain appropriate drug levels in the blood or tissues. For potent drugs, one must avoid dumping of drugs in a short period (short Tmax) from the delivery device into the gastro-intestinal tract so that one can avoid erratic blood levels for the medicament.

The medicament, if insoluble, forms a suspension in the capsule composition. The medicament may dissolve in the capsule composition and in some cases, the medicament may form an ion-pair bond with the reactive groups in the polymer or the excipients used to prepare the capsule composition. The medicament can be covalently bound to the polymer or the excipients used to prepare the capsule composition. The chemical bond can be of any nature—peptide, an ester or other kinds. Upon administration of the hard shell capsule orally, the capsule may stay intact till it reaches the gastro-intestinal tract. In some cases, the hard shell may disintegrate or dissolve in the mouth cavity releasing the drug (orally disintegrating or dissolving capsule). The release of drug which is embedded in the capsule shell is controlled by three mechanisms—diffusion through the shell matrix, hydrolysis of medicament-polymer chemical bond or by dissolution of the hard capsule shell to release the dissolved drug. In an embodiment, multiple drugs can be incorporated in the capsule shell which could be released with different mechanisms.

Figure 3:
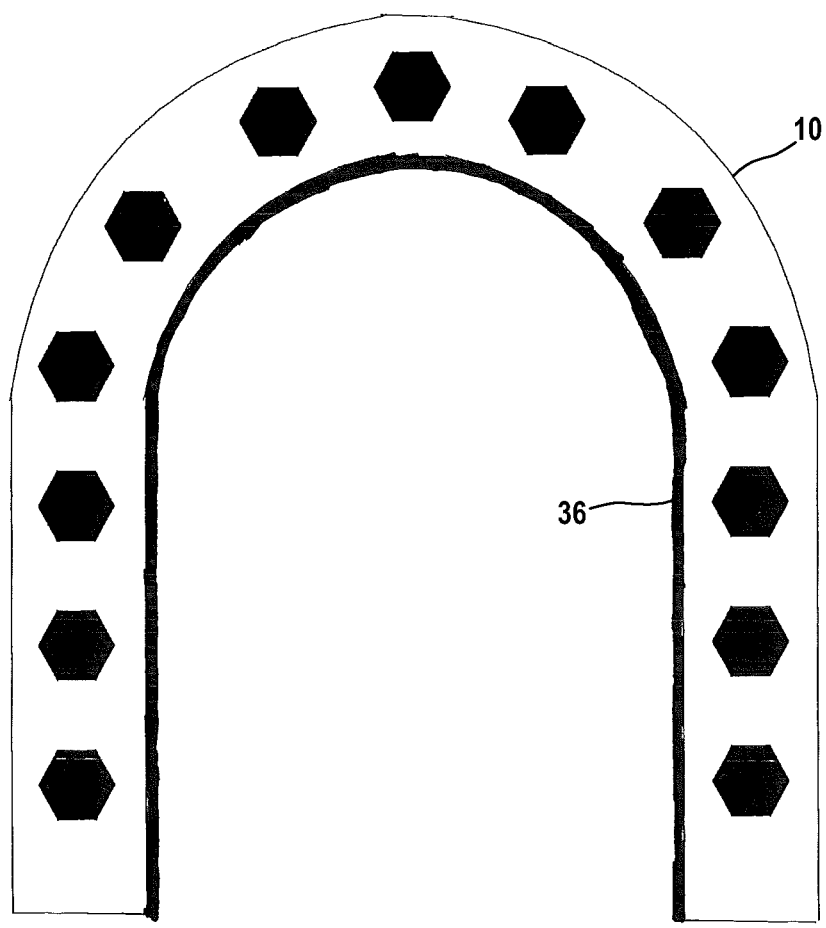
FIG. 3 illustrates the cap shown in FIG. 1 with a coating or film deposited on the inside of the cap.
Figure 4:
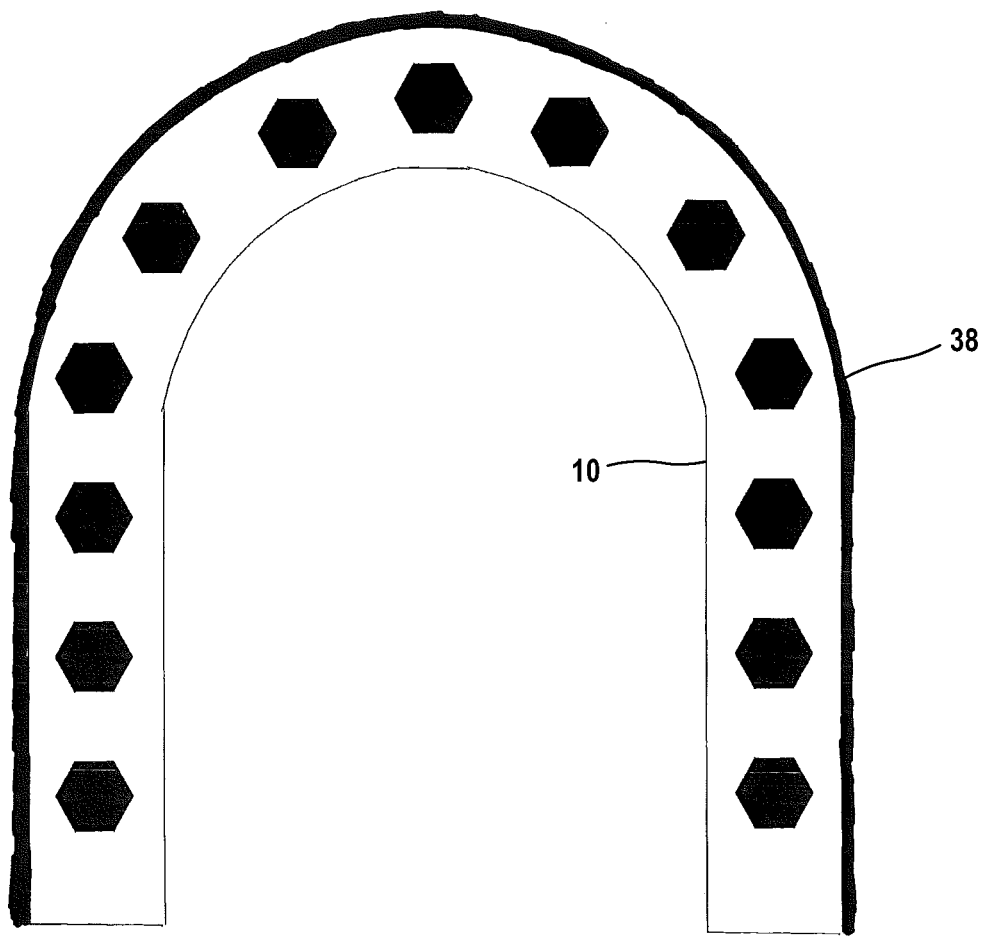
FIG. 4 illustrates the cap shown in FIG. 1 with a coating or film deposited on the outside of the cap.

In another embodiment, a drug-loaded laminated empty hard shell capsule is prepared using the double pin-dip method. The drug-loaded polymer layer can be the inner or outer layer. If the drug-loaded capsule shell layer is on the inside, the outside capsule shell layer may act as enteric coating or a swellable in nature to control the drug release. FIG. 4 illustrates an enteric coating 38 on the outside of the cap 10. In the drug-loaded layer is on the outside, the inside capsule shell layer can act as a barrier between the medicaments in the core of the capsule and medicaments which is in the outside drug-loaded capsule shell layer. FIG. 3 illustrates the inside capsule shell layer or coating 36 on the inside of the cap 10.

Medicaments placed in the capsule core can be in the form of powders, granules, beads, pellets, mini-tablets and mini-capsules.

With the following examples, one skilled in the art, can understand and use the present invention.

EXAMPLE 1

Entecavir (0.5 mg) in the Capsule Shell and Tenofovir (300 mg) in the Core for the Chronic Hepatitis B Treatment A capsule shell composition containing gelatin and other excipients is prepared to which a suitable amount of entecavir is added. The capsules are prepared using the pin-dip method. Here, entecavir (0.5 mg) is physically incorporated in size '0' hard gelatin capsule shells. FIG. 2 illustrates the entecavir 16 dispersed throughout the cap 10 and the body 12 forming the capsule 14. Tenofovir pellets are prepared using a conventional method and the pellets 34 (see FIG. 2) equivalent to a 300 mg dose are filled in the capsule shells loaded with entecavir.

EXAMPLE 2

Clonidine (75 microgram) in the Capsule Shell and Bupivacaine (10 mg) in the Core for Labor Pain Polymer such as polymethacrylic acid (RCOOH) is first converted to RCOCl form, which can react with clonidine in a suitable solvent system. The polymeric prodrug of clonidine is dissolved in an aqueous medium along with suitable excipients (plasticizer, coloring agent etc.) to form a solution. Hard capsule shells are prepared using a pin-dip method known to those skilled in the art. The amount of clonidine per unit is 75 micrograms. Bupivacaine granules are prepared using a conventional method and are filled in the hard capsule shells containing clonidine. The dose of bupivacaine is 10 mg per capsules. In this case, bupivacaine is released upon dissolution of the hard capsule shell. Clonidine is released after the hydrolysis of ester bonds of the polymeric prodrug.

EXAMPLE 3

Ethinyl Estradiol (30 microgram) and Drosperenone (3 mg) in the Capsule Shell and Thalidomide (200 mg) in the Core In this case, ethinyl estradiol bears a phenolic OH, which can form an ester bond with RCOOH (for example, with carboxymethyl cellulose). The polymeric prodrug of ethinyl estradiol is dissolved in an aqueous system along with necessary excipients for the capsule composition. Drosperenone is suspended in this solution along with other excipients and hard capsule shells are manufactured using the pin-dip method. Thalidomide granules are prepared using a conventional technique. The granules are filled in the ethinyl estradiol/drosperenone-loaded capsule shells to produce a combination capsule dosage form.

EXAMPLE 4

Omeprazole (10 mg) in the Capsule Shell and Pancrelipase (6000 to 24,000 USP Units of Lipase) in Core Hard gelatin capsule shells are prepared with physically distributing omeprazole (10 mg per capsule) using techniques described earlier. This drug-loaded shell is further coated with cellulose acetate phthalate (enteric coating). Spheres, 1 to 2 mm, of pancrelipase is prepared using conventional methods known to skilled in the art. For example, the spheres can be prepared using cethyl alcohol, dimethicone, polyethylene glycol and triethyl citrate. The spheres of pancrelipase are filled in the omeprazole-loaded hard capsule shells, which are enteric coated. Omeprazole and pancrelipase formulations, being susceptible to stomach acids, are typically enteric coated.

Figure 5:
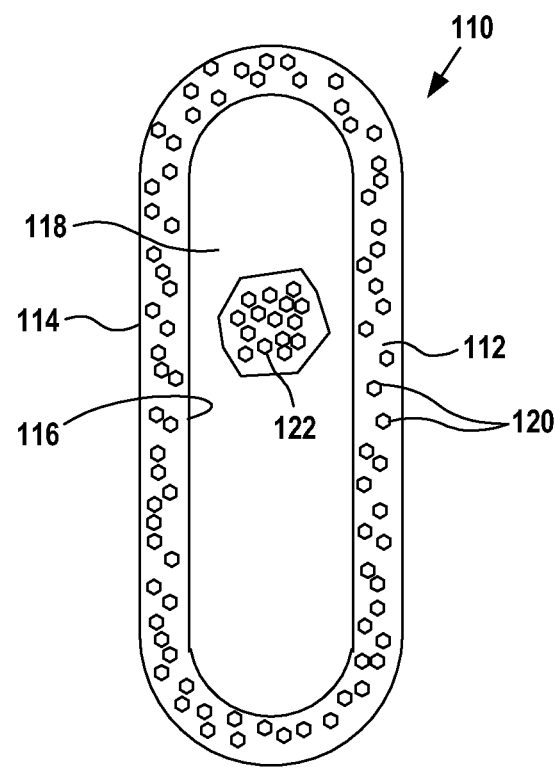
FIG. 5 illustrates a soft gelatin capsule in accordance with the present invention.

FIG. 5 illustrates a soft gelatin capsule 110 in accordance with the present invention. The soft capsule 110 is formed from a composition 112 and has an outer surface 114 and an inner surface 116, the inner surface 116 surrounding an interior volume or cavity 118.

Dispersed throughout the composition 112 between the outer and inner surfaces 114, 116 are drug molecules 120. The drug molecules 120 can be physically or molecularly distributed throughout the composition 112 as previously described for the hard-shell capsule 14.

The soft gelatin capsule 110 may optionally hold an additional solid, liquid, or capsulated drug or pharmaceutical material 122 in the capsule interior 118 as is known in the art.

From the foregoing, it will be seen that this invention opens up several possibilities using the empty, hard capsule shell as a carrier of different medicaments along with a different set of drugs in the core. While specific examples have been presented here, various modifications can be made and the invention is not limited to the examples shown in this patent application.

What is claimed is:

1. A hard-shell capsule comprising:
   a body, a cap, a first drug, and a second drug;
   the body and the cap cooperatively defining a hollow capsule; and
   the first drug being dispersed only throughout the cap and the second drug being dispersed only throughout the body.

2. The hard-shell capsule of claim 1 wherein at least one of the said cap and said body comprises a composition and the drug is physically disbursed throughout the composition.

3. The hard-shell capsule of claim 1 wherein at least one of the said cap and said body comprises a composition and the drug is chemically bonded with said composition.

4. The hard-shell capsule of claim 1 wherein at least one of the said body and said cap is manufactured by a pin dipping technique wherein a pin is dipped into a liquid.

* * * * *